(12) United States Patent
Daniels et al.

(10) Patent No.: US 6,982,052 B2
(45) Date of Patent: Jan. 3, 2006

(54) PROCESS AND APPARATUS FOR AIR FORMING AN ARTICLE HAVING A PLURALITY OF SUPERIMPOSED FIBROUS LAYERS

(75) Inventors: Susan J. Daniels, Neenah, WI (US); David W. Heyn, Neenah, WI (US); Derek Paul Murphy, Menasha, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 208 days.

(21) Appl. No.: 10/255,660

(22) Filed: Sep. 26, 2002

(65) Prior Publication Data

US 2004/0061263 A1 Apr. 1, 2004

(51) Int. Cl.
*B29C 59/00* (2006.01)
*B29C 59/02* (2006.01)
*B29C 69/00* (2006.01)

(52) U.S. Cl. .................. 264/101; 264/113; 264/118; 264/138; 264/145; 264/162; 264/172.19; 264/173.1; 425/81.1; 425/83.1; 425/218; 425/220; 425/405.1

(58) Field of Classification Search ............... 264/101, 264/113, 118, 138, 145, 162, 172.19, 173.1; 425/81.1, 83.1, 218, 220, 405.1
See application file for complete search history.

(56) References Cited

U.S. PATENT DOCUMENTS

| | | |
|---|---|---|
| 2,161,539 A | 6/1939 | Swartz |
| 2,964,039 A | 12/1960 | Johnson, Jr. et al. |
| 3,085,309 A | 4/1963 | Olson |

(Continued)

FOREIGN PATENT DOCUMENTS

| | | |
|---|---|---|
| AU | 458424 | 2/1975 |
| DE | 198 23 954 A1 | 12/1999 |
| EP | 0 151 018 A2 | 8/1985 |
| EP | 0 226 939 A2 | 12/1986 |
| EP | 0 297 180 B1 | 1/1989 |
| EP | 0 298 348 A1 | 11/1989 |
| EP | 0 399 511 A2 | 11/1990 |

(Continued)

OTHER PUBLICATIONS

International Search Report, dated May 28, 2003 in PCT/US 03/00881, 8 pages.
International Search Report for PCT/US 03/00293 dated Jul. 29, 2003.
International Search Report for PCT/US 03/01337 dated Jul. 30, 2003.
International Search Report for PCT/US 03/16480 dated Oct. 2, 2003.
Partial International Search Report for PCT/US 03/15959, dated Oct. 16, 2003.
International Search Report for PCT/US 03/16480 dated Oct. 2, 2003.
International Search Report for PCT/US2004/008428 dated Aug. 23, 2004, 4 pages.
International Search Report for PCT/US2004/006915 dated Nov. 5, 2004, 7 pages.

*Primary Examiner*—Stephen J. Lechert, Jr.
(74) *Attorney, Agent, or Firm*—Senniger Powers

(57) ABSTRACT

Process and apparatus for air forming an article having a plurality of superimposed fibrous layers. The layers are formed in substantially discrete forming chambers by depositing fibrous material on a forming surface which moves along an arcuate path through the chambers. A first layer is air-formed on the forming surface as the surface moves through the first forming chamber and a second layer is air-formed over the first layer as the surface moves through the second forming chamber.

46 Claims, 9 Drawing Sheets

U.S. PATENT DOCUMENTS

| | | | |
|---|---|---|---|
| 3,156,751 A | 11/1964 | Valdes et al. | |
| 3,587,579 A | 6/1971 | Sabee | |
| 3,629,047 A | 12/1971 | Davison | |
| 3,683,921 A | 8/1972 | Brooks et al. | |
| 3,768,479 A | 10/1973 | Widlund | |
| 3,816,231 A | 6/1974 | Marshall | |
| 3,856,012 A | 12/1974 | MacDonald et al. | |
| 3,862,877 A | 1/1975 | Camden | |
| 3,867,935 A | 2/1975 | Eisdorfer et al. | |
| 3,888,248 A | 6/1975 | Moore et al. | |
| 3,935,979 A | 2/1976 | Hickey | |
| 4,001,472 A | 1/1977 | Thomas et al. | |
| 4,028,455 A | 6/1977 | Ueda et al. | |
| 4,141,772 A | 2/1979 | Buell | |
| 4,217,078 A | 8/1980 | Buell | |
| 4,235,237 A | 11/1980 | Mesek et al. | |
| 4,300,562 A | 11/1981 | Pieniak | |
| 4,303,189 A | 12/1981 | Wiley et al. | |
| 4,392,862 A | 7/1983 | Marsan et al. | |
| 4,425,127 A | 1/1984 | Suzuki et al. | |
| 4,606,964 A | 8/1986 | Wideman | |
| 4,666,647 A | 5/1987 | Enloe et al. | |
| 4,674,966 A | 6/1987 | Johnson et al. | |
| 4,704,112 A | 11/1987 | Suzuki et al. | |
| 4,710,185 A | 12/1987 | Sneyd, Jr. et al. | |
| 4,761,258 A | 8/1988 | Enloe | |
| 4,764,325 A | 8/1988 | Angstadt | |
| 4,765,780 A | 8/1988 | Angstadt | |
| 4,773,903 A | 9/1988 | Weisman et al. | |
| 4,775,579 A | 10/1988 | Hagy et al. | |
| 4,810,568 A | 3/1989 | Buyofsky et al. | |
| 4,837,715 A | 6/1989 | Ungpiyakul et al. | |
| 4,904,440 A | 2/1990 | Angstadt | |
| 4,908,175 A | 3/1990 | Angstadt | |
| 4,915,897 A | 4/1990 | Farrington et al. | |
| 4,915,993 A | 4/1990 | Ten Wolde | |
| 4,927,346 A | 5/1990 | Kaiser et al. | |
| 4,927,582 A | 5/1990 | Bryson | |
| 5,004,579 A | 4/1991 | Wislinski et al. | |
| 5,017,324 A | 5/1991 | Kaiser et al. | |
| 5,124,188 A | 6/1992 | Roe et al. | |
| 5,128,082 A | 7/1992 | Makoui | |
| 5,139,841 A | 8/1992 | Makoui et al. | |
| 5,144,729 A | 9/1992 | Austin et al. | |
| 5,161,283 A | 11/1992 | Hansen | |
| 5,219,633 A | 6/1993 | Sabee | |
| 5,281,208 A | 1/1994 | Thompson et al. | |
| 5,302,445 A | 4/1994 | DePetris et al. | |
| 5,328,072 A | 7/1994 | Ruessmann et al. | |
| 5,334,446 A | 8/1994 | Quantrille et al. | |
| 5,389,095 A | 2/1995 | Suzuki et al. | |
| 5,389,202 A | 2/1995 | Everhart et al. | |
| 5,429,788 A * | 7/1995 | Ribble et al. | 264/510 |
| 5,447,677 A | 9/1995 | Griffoul et al. | |
| 5,466,409 A | 11/1995 | Partridge et al. | |
| 5,486,167 A | 1/1996 | Dragoo et al. | |
| 5,505,720 A | 4/1996 | Wallers et al. | |
| 5,527,300 A | 6/1996 | Sauer | |
| 5,531,729 A | 7/1996 | Coles et al. | |
| 5,591,148 A | 1/1997 | McFall et al. | |
| 5,607,415 A | 3/1997 | Datta et al. | |
| 5,614,283 A | 3/1997 | Potnis et al. | |
| 5,622,581 A | 4/1997 | Ducker et al. | |
| 5,672,306 A | 9/1997 | Sprang et al. | |
| 5,704,931 A | 1/1998 | Holtman et al. | |
| 5,756,039 A | 5/1998 | McFall et al. | |
| 5,762,844 A | 6/1998 | Van Himbergen et al. | |
| 5,772,813 A | 6/1998 | Bitowft et al. | |
| 5,803,334 A | 9/1998 | Patel et al. | |
| 5,818,719 A | 10/1998 | Brandon et al. | |
| 5,866,173 A | 2/1999 | Reiter et al. | |
| 5,871,613 A | 2/1999 | Bost et al. | |
| 5,873,963 A | 2/1999 | Trombetta et al. | |
| 5,902,757 A | 5/1999 | Stern et al. | |
| 5,916,661 A | 6/1999 | Benson et al. | |
| 5,925,439 A | 7/1999 | Haubach | |
| 5,938,648 A | 8/1999 | LaVon et al. | |
| 5,944,706 A | 8/1999 | Palumbo et al. | |
| 5,947,945 A | 9/1999 | Cree et al. | |
| 5,961,509 A | 10/1999 | Kling | |
| 5,997,520 A | 12/1999 | Ahr et al. | |
| 6,048,489 A | 4/2000 | Reiter et al. | |
| 6,060,637 A | 5/2000 | Bitowft et al. | |
| 6,107,538 A | 8/2000 | Young et al. | |
| 6,203,654 B1 | 3/2001 | McFall et al. | |
| 6,204,207 B1 | 3/2001 | Cederblad et al. | |
| 6,220,999 B1 | 4/2001 | Kugler et al. | |
| 6,258,996 B1 | 7/2001 | Goldman | |
| 6,262,331 B1 | 7/2001 | Nakahata et al. | |
| 6,284,943 B1 | 9/2001 | Osborn, III et al. | |
| 6,296,862 B1 | 10/2001 | Paul et al. | |
| 6,330,735 B1 | 12/2001 | Hahn et al. | |
| 6,375,644 B2 | 4/2002 | Mizutani | |
| 6,416,697 B1 | 7/2002 | Venturino et al. | |
| 6,492,574 B1 | 12/2002 | Chen et al. | |
| 6,533,978 B1 * | 3/2003 | Wisneski et al. | 264/113 |
| 6,533,989 B1 * | 3/2003 | Wisneski et al. | 264/510 |
| 6,630,096 B2 | 10/2003 | Venturino et al. | |
| 2001/0039405 A1 | 11/2001 | Keuhn et al. | |
| 2003/0116888 A1 | 6/2003 | Rymer et al. | |
| 2003/0119401 A1 | 6/2003 | Chakravarty et al. | |
| 2003/0132556 A1 | 7/2003 | Venturino et al. | |
| 2003/0139721 A1 | 7/2003 | Melius et al. | |
| 2004/0092898 A1 | 5/2004 | Schaffer et al. | |
| 2004/0102752 A1 | 5/2004 | Chen et al. | |

OTHER PUBLICATIONS

| | | |
|---|---|---|
| EP | 0 467 409 A1 | 1/1992 |
| GB | 2168612 A | 6/1986 |
| JP | 09122172 | 5/1997 |
| JP | 10211236 | 8/1998 |
| WO | WO 93/18729 A1 | 9/1993 |
| WO | WO 96/00550 A1 | 1/1996 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 00/63479 A1 | 10/2000 |
| WO | WO 01/92003 A1 | 12/2001 |
| WO | WO 03/059232 A2 | 7/2003 |

* cited by examiner

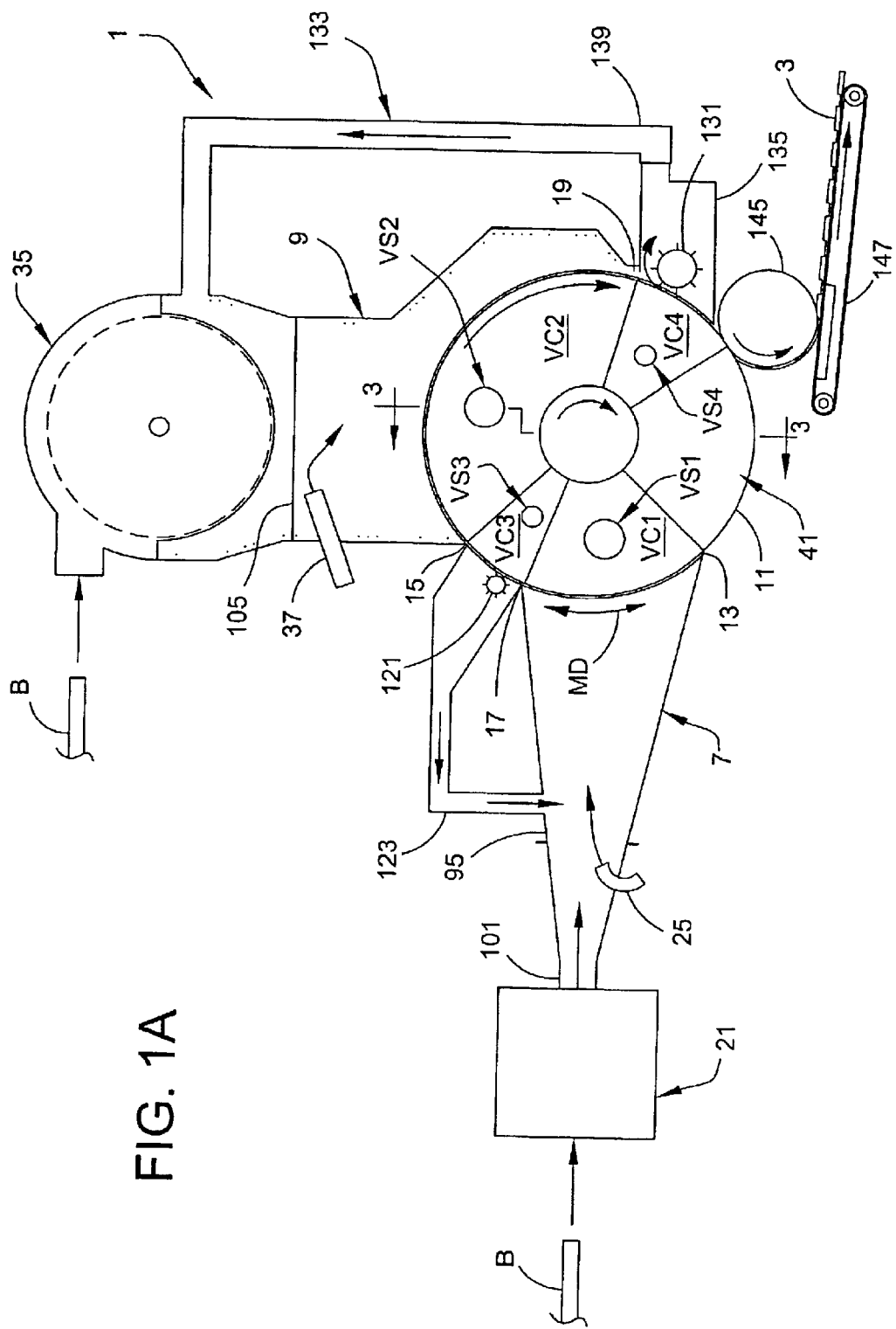

PROCESS AND APPARATUS FOR AIR FORMING AN ARTICLE HAVING A PLURALITY OF SUPERIMPOSED FIBROUS LAYERS

BACKGROUND OF THE INVENTION

This invention relates generally to a process and apparatus for making an air formed article having more than one layer, and especially to a fibrous web and an absorbent core formed by such a web. The absorbent core can be used for applications such as disposable diapers, child's training pants, feminine care articles, incontinence articles, and the like.

In the general practice of forming fibrous articles, it has been common to use a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous member, such as an absorbent core to be used as part of one of the aforementioned articles. An absorbent core formed in this fashion has a liquid holding formation which is intended to be the primary repository for liquid to be held by the absorbent core. Thus, the liquid holding formation has conventionally been formed to have a greater amount of fibrous and superabsorbent material (SAM) than surrounding regions and is generally thicker than the surrounding regions of fibrous material. In addition, bonding agents or other strengthening components may be incorporated to provide a stabilized absorbent member. The absorbent member may then be stored or immediately directed for further processing and assembly with other components to produce an absorbent article. Other conventional techniques, such as dry-forming techniques, wet-laying techniques, foam-forming techniques, and various wet-forming techniques, have also been employed to form stabilized absorbent members. The resulting absorbent members have included absorbent fibers, natural fibers, synthetic fibers, superabsorbent materials, binders, and strengthening components in desired combinations.

Some absorbent members are formed as a laminate, i.e., a structure having two or more layers. Conventional systems capable of making such articles typically comprise two or more complete independent forming systems, one system for forming each layer after which the layers are combined to make the article. Because the fibers are not substantially commingled at the interface between adjacent layers, the flow of liquid across the interface is inhibited, which is undesirable. The use of such systems also typically requires a large capital expenditure, and space requirements make such systems costly and often undesireable. Further, the implementation of two forming systems requires phase adjustments between the two systems to ensure that the product components by the systems are in proper registration with respect to one another in the final product. If the systems are out of phase, defective products are manufactured and waste is induced, further increasing manufacturing costs.

SUMMARY OF THE INVENTION

Apparatus of the present invention is used for air forming an article having a plurality of superimposed fibrous layers. The apparatus comprises first and second substantially discrete forming chambers, and a foraminous forming surface movable through the first and second forming chambers along a forming path length. A first fiber feed mechanism is provided for introducing a fibrous material into the first forming chamber. A first vacuum source in communication with the first forming chamber is adapted for drawing fibrous material in the first forming chamber onto the forming surface to form a first layer on the forming surface. A first removing and directing mechanism is operable for removing a portion of the first layer and directing the portion removed back into the first forming chamber. A second fiber feed mechanism is provided for introducing a fibrous material into the second forming chamber. A second vacuum source in communication with the second forming chamber is adapted for drawing fibrous material in the second forming chamber onto the forming surface to form a second layer on the forming surface superimposed on the first layer.

A process of the present invention is used for forming an article having a plurality of superimposed fibrous layers. The process comprises moving a foraminous forming surface through first and second substantially discrete forming chambers along a forming path length, introducing a fibrous material into the first forming chamber, and vacuum drawing fibrous material in the first forming chamber onto the forming surface to form a first layer on the forming surface. The process also involves removing a portion of the first layer and directing the portion removed back into the first forming chamber. Fibrous material introduced into the second forming chamber is also vacuum drawn onto the forming surface to form a second layer on the forming surface superimposed on the first layer.

In another embodiment, the forming surface comprises a plurality of faraminous areas spaced at intervals along the forming surface, each foraminous area having a first section for collecting fibrous material to a first depth and a second section for collecting fibrous material to a second depth greater than said first depth. In this embodiment, the process involves introducing a fibrous material into the first forming chamber, and vacuum drawing fibrous material in the first forming chamber onto the forming surface to form a first layer on the first and second sections of the forming areas. The process further comprises introducing a fibrous material into the second forming chamber, and vacuum drawing fibrous material in the second forming chamber onto the forming surface to form a second layer on the first and second sections of the forming areas, the second layer being superimposed on the first layer.

Other objects and features will be in part apparent and in part pointed out hereinafter.

BRIEF DESCRIPTION OF THE DRAWINGS

FIG. 1A is a view similar to FIG. 1 but showing a second embodiment of the apparatus;

Corresponding reference characters indicated corresponding parts throughout the several views of the drawings.

DETAILED DESCRIPTION OF THE DRAWINGS

Figure 1:
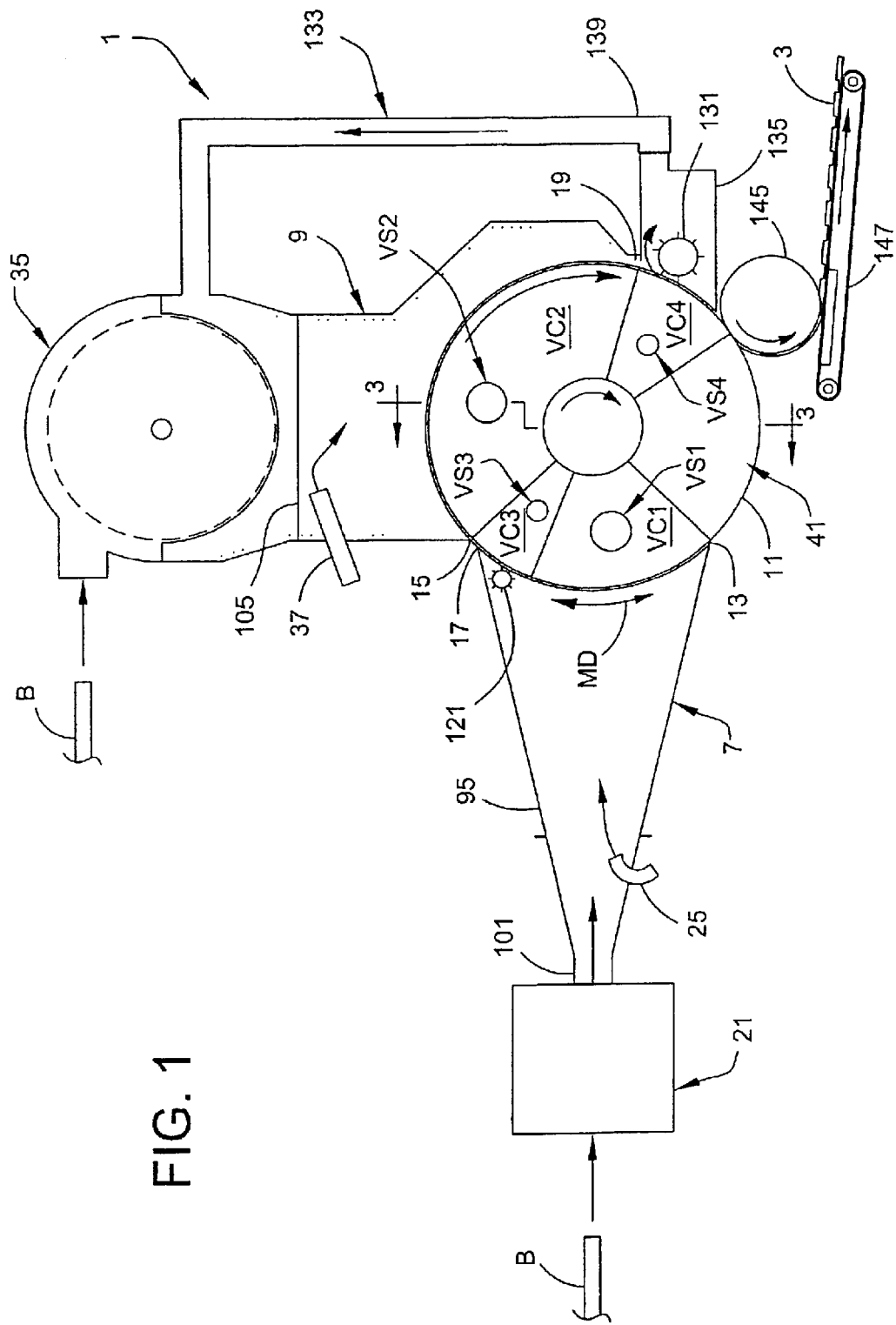
FIG. 1 is a schematic, side elevation of apparatus for forming multiple-layer fibrous articles.

The present invention is generally directed to a process and apparatus, indicated generally as 1 in FIG. 1, for making a fibrous article 3, comprising multiple layers of fibrous material and/or other particulate material. In particular aspects, the article 3 can be an absorbent member used as an absorbent core within disposable personal care products such as diapers, children's training pants, adult incontinence products, feminine care products, medical garments, bandages and the like. As described herein, the article 3 has two layers, designated L1 and L2, but it will be understood that the present invention can be employed to form a member with more than two layers.

For the purpose of describing the present invention, the apparatus 1 has an appointed machine-direction MD (FIG. 1) extending generally in a direction that the absorbent member, or a particular component or material thereof, is transported along and through a particular, local position of the apparatus. A cross-machine direction CD (FIG. 3) of the apparatus 1 lies generally within the plane of the article 3, or particular component or material thereof, and is transverse to the machine-direction MD. A Z-direction ZD of the apparatus 1 is substantially perpendicular to both the machine-direction MD and the cross-machine direction CD, and extends generally along a depth-wise, thickness dimension of the article 3 formed by the apparatus.

In general, apparatus 1 comprises first and second substantially discrete forming chambers, designated 7 and 9, respectively, and a foraminous forming surface 11 movable through the two chambers along a forming path P. The first and second chambers have entrances designated 13 and 15, respectively, where the forming surface 11 enters the chambers, and exits designated 17 and 19, respectively, where the forming surface exits the chambers. As used herein, the "forming path length" means the length of the path P from the entrance 13 of the first forming chamber 7 to the exit 19 of the second forming chamber 9. (If more than two forming chambers are used, the forming path length is the length of the forming path P from the entrance 13 of the first forming chamber 7 to the exit of the last forming chamber along the path.) The apparatus 1 also includes a first fiber feed mechanism 21 for introducing a fibrous material into the first forming chamber 7, and a first superabsorbent feed mechanism 25 for introducing a superabsorbent material into the first forming chamber. A first vacuum source, generally indicated at VS1, communicates with the first forming chamber 7 for drawing fibrous material and superabsorbent material in the first forming chamber onto the forming surface 11 to form a first layer L1 on the forming surface. In accordance with one aspect of the present invention, the apparatus 1 further comprises a second fiber feed mechanism 35 for introducing a fibrous material into the second forming chamber 9, and a second superabsorbent feed mechanism 37 for introducing a superabsorbent material into the second forming chamber 9. A second vacuum source, generally designated VS2, communicates with the second forming chamber 9 for drawing fibrous material and superabsorbent material in the second forming chamber onto the forming surface 11 to form a second layer L2 on the forming surface superimposed on the first layer. Third and fourth vacuum sources VS3, VS4 are also provided for holding one or both layers L1, L2 on the forming surface 11 as it moves, as will be described in more detail hereinafter.

Figure 3:
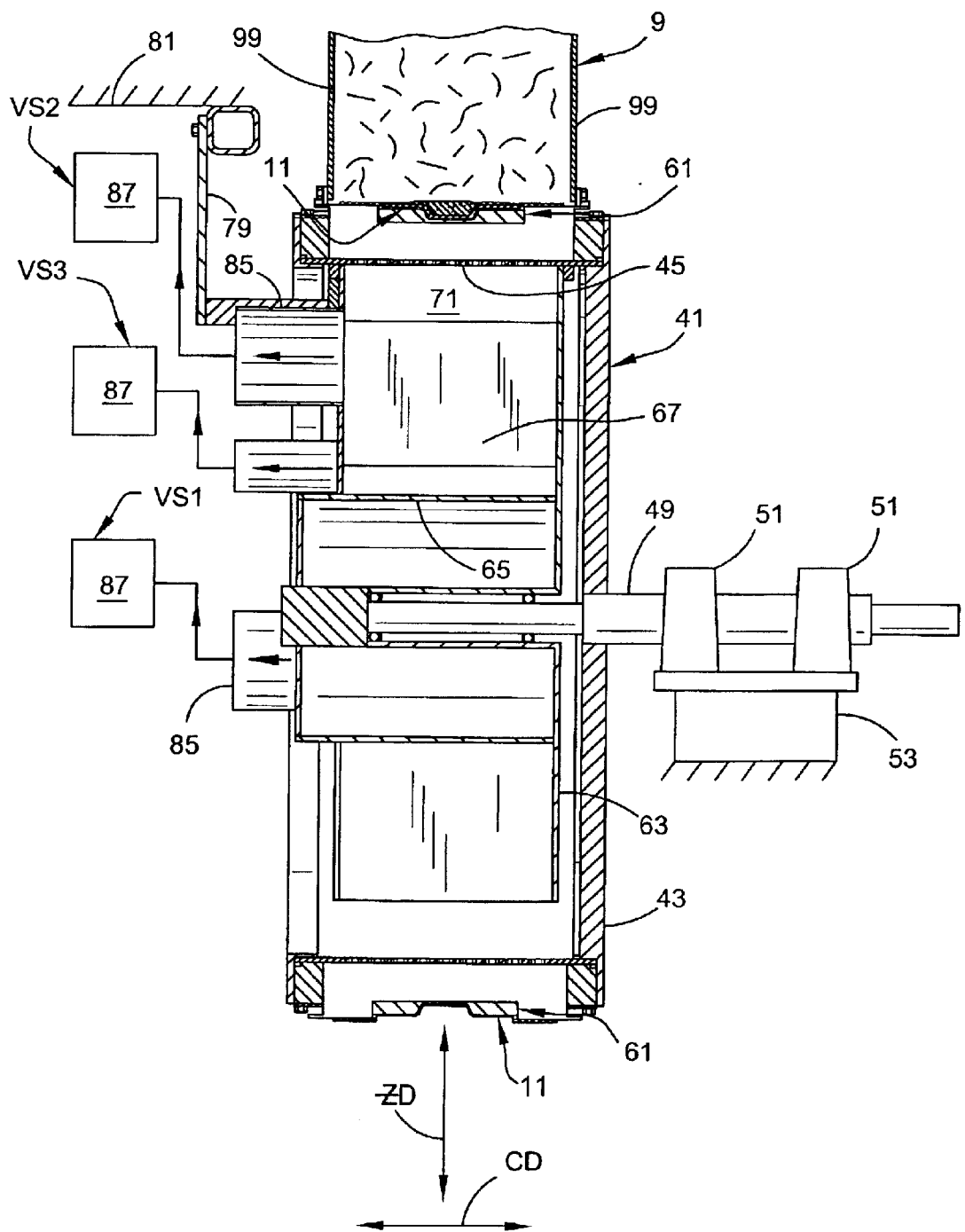
FIG. 3 is an enlarged sectional view taken in the plane of 3—3 of FIG. 1.
Figure 4:
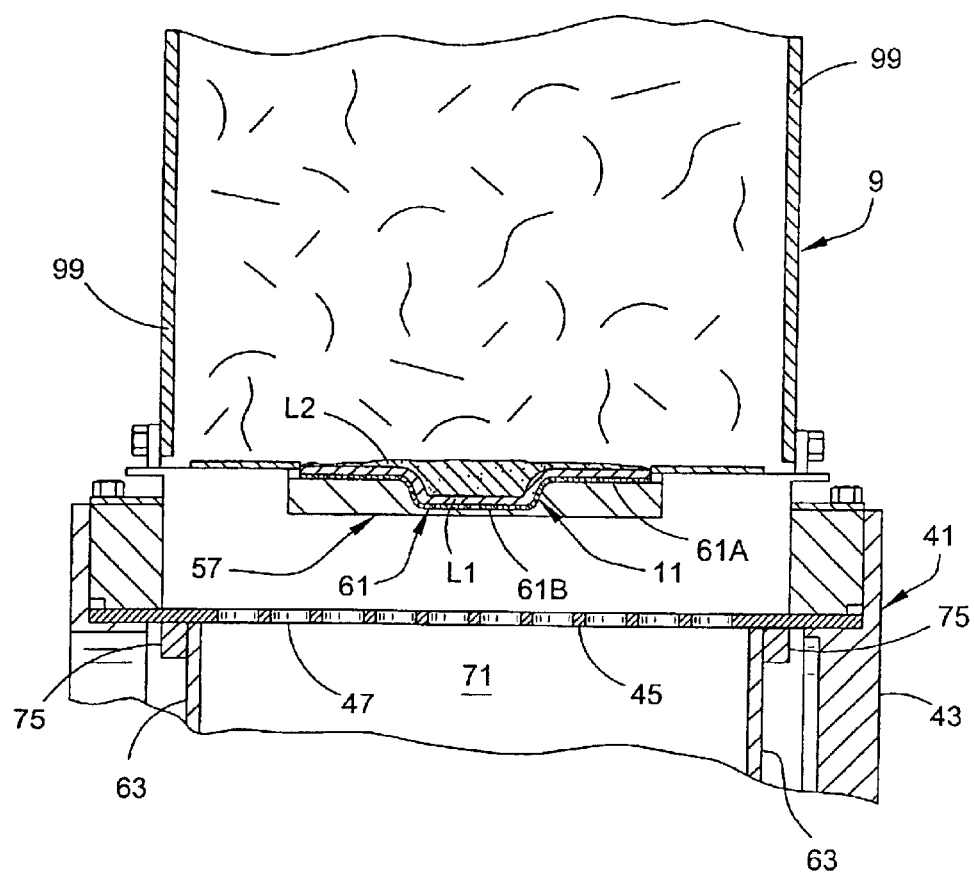
FIG. 4 is an enlarged sectional view taken in the plane of 4—4 of FIG. 2.

In the preferred embodiment, the foraminous forming surface 11 extends around the circular circumference of a drum 41. As illustrated in FIGS. 3 and 4, the drum 41 includes a circular wall 43 and an outer annular rim 45 extending as a cantilever from the wall for supporting the forming surface 11. The drum rim has a multiplicity of holes 47 over its surface area to provide a substantially free movement of fluid, such as air, through the thickness of the rim. The drum is rotatably mounted on a shaft 49 connected by bearings 51 to a support 53. The shaft 49 is rotatably driven by a suitable motor or line shaft (not shown) in a clockwise direction in the illustrated embodiment of FIG. 1.

Figure 5:
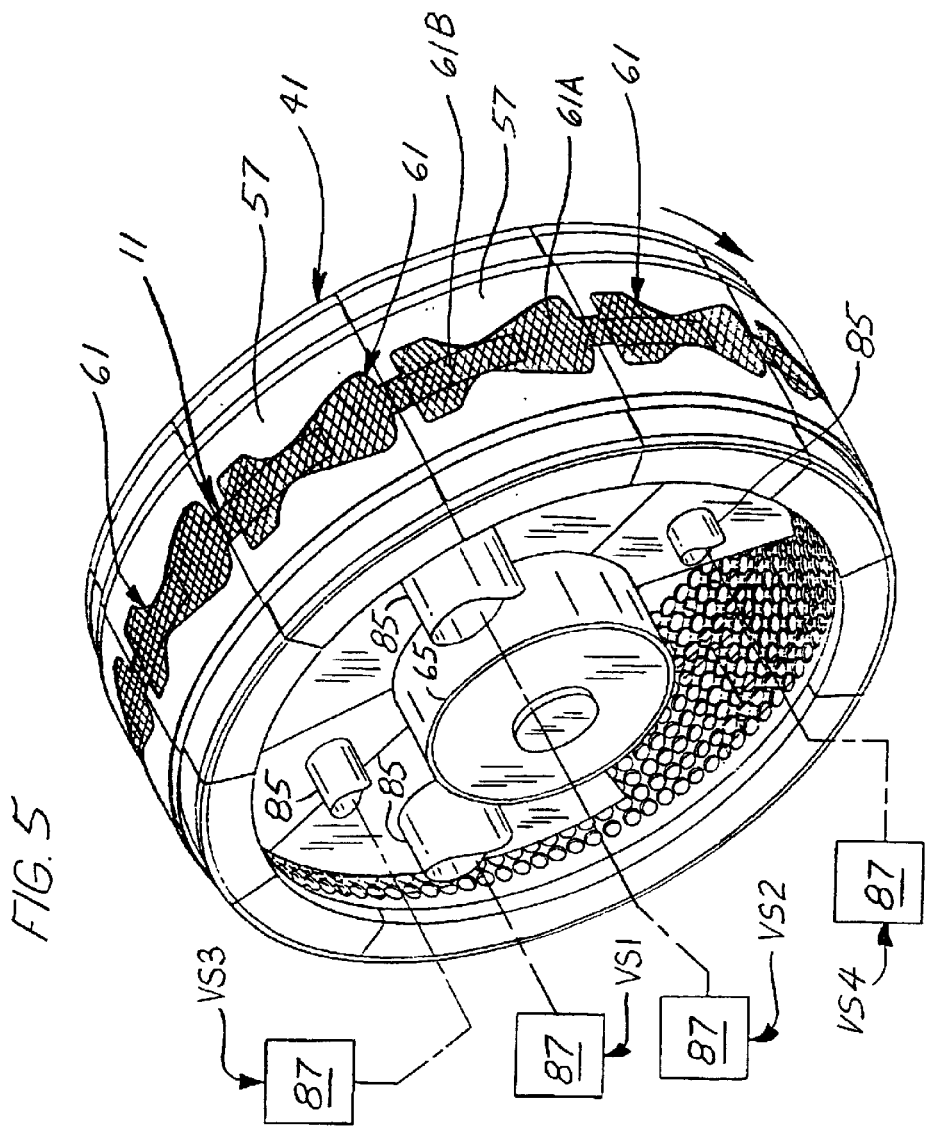
FIG. 5 is a schematic perspective of a forming drum of the apparatus of FIG. 1.

The foraminous forming surface 11 is defined in the illustrated embodiment (FIG. 5) by a series of form members 57 which are arranged end-to-end around the periphery of the forming drum 41 and independently attached to the drum. As may be seen in FIG. 5, each form member 57 has a formaminous area 61 fabricated from wire mesh or the like defining a pattern in which fibrous material is collected. The patterns on the form members are preferably substantially identical and correspond to a desired shape of individual articles 3 which repeats over the circumference of the drum 41. However, partially repeating or non-repeating pattern shapes may be used with the present invention. It is also understood that a continuous, un-patterned article may be formed on the forming surface, such as where the forming surface is flat or where the formed article is generally rectangular, and is subsequently processed (e.g., cut or otherwise formed) to a desired shape. In the embodiment shown in FIGS. 4 and 5, each foraminous area 61 has a first section 61A for collecting fibrous material to a first depth and second section or pocket 61B for collecting fibrous material to a second depth greater than the stated first depth. The material collected in the pocket section 61B typically constitutes a liquid holding formation intended to be the primary repository for liquid to be held by the article.

For additional detail regarding the construction of an exemplary forming surface, reference may be made to pending U.S. patent application Ser. No. 10/207,929; entitled APPARATUS AND FORM FOR MAKING AN AIR FORMED FIBROUS WEB by Daniels et al., filed Jul. 30, 2002, U.S. patent application Ser. No. 09/694,374, entitled FORMING MEDIA WITH ENHANCED AIR FLOW PROPERTIES by Michael B. Venturino et al., filed Oct. 23, 2000, and to U.S. Pat. No. 6,330,735, entitled APPARATUS AND PROCESS FOR FORMING A LAID FIBROUS WEB WITH ENHANCED BASIS WEIGHT CAPABILITY, by John Timothy Hahn et al., assigned to Kimberly-Clark Worldwide, Inc., the entire disclosures of which are incorporated by reference in a manner consistent herewith. It will be understood, however, that the principles of the present invention can be practiced with different foraminous forming surfaces.

The forming surface 11 is illustrated herein as being part of the forming drum 41, but it is to be understood that other techniques for providing the foraminous forming surface 11 may also be employed without departing from the scope of the present invention. For example, the forming surface may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

Figure 6:
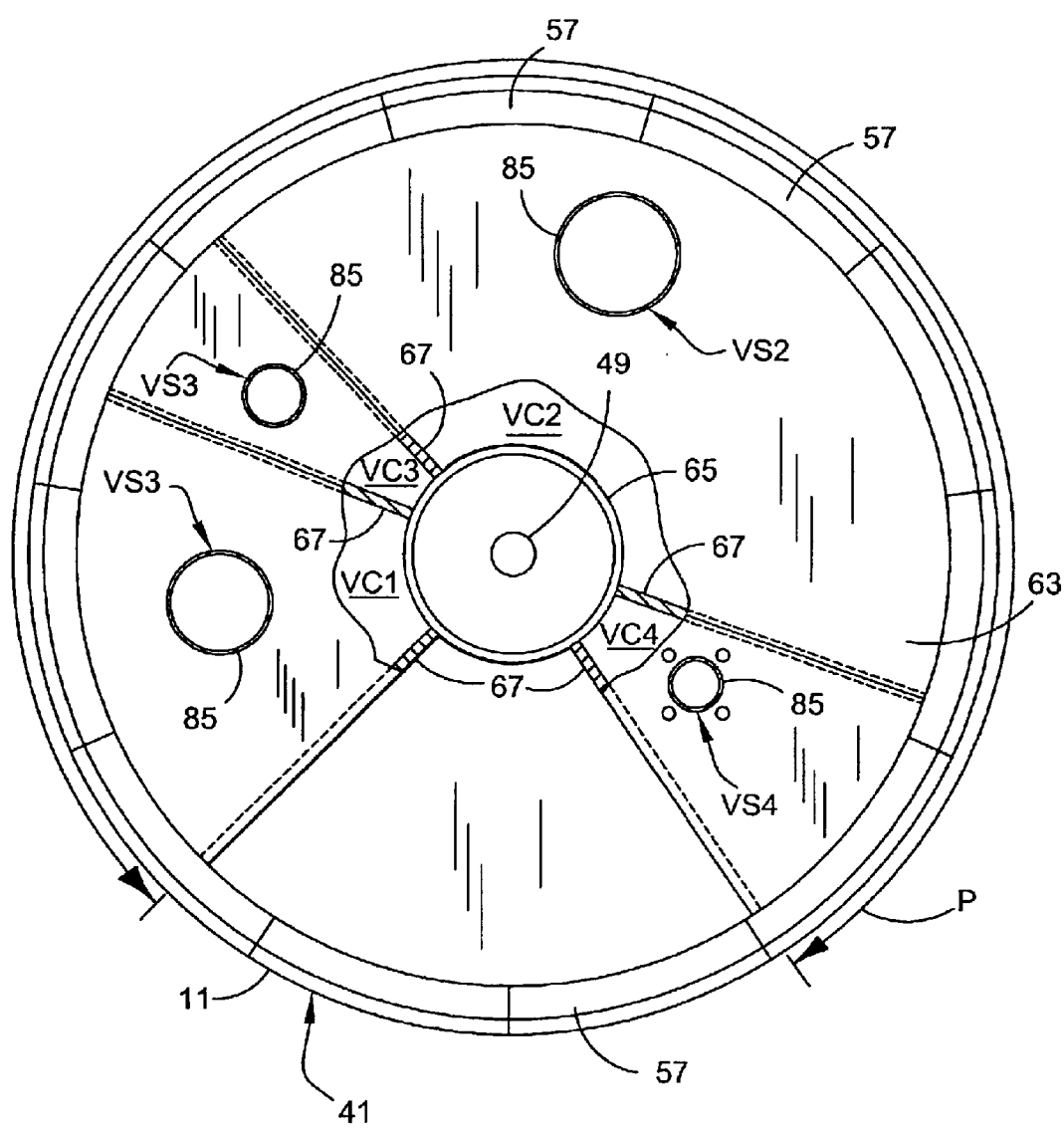
FIG. 6 is a schematic side elevation of the forming drum with portions broken away to show interior construction.

As illustrated in FIG. 6, the four vacuum sources VS1–VS4 comprise a plurality of vacuum chambers VC1, VC2, VC3 and VC4, respectively, on the inside of the drum 41 extending over respective arcuate segments of the aforementioned forming path P. The vacuum chambers VC1–VC4 are defined by structure comprising, in one embodiment (FIGS. 3–6), a pair of spaced apart side walls 63 extending generally parallel to the drum wall 43 on the inside of the drum 41, a cylindric central hub 65 connecting the side walls 63, and a series of radial partitions or dividers 67 between the side walls extending radially from the central hub 65 to adjacent the rim 45 of the drum and forming the end walls of the chambers VC1–VC4. Each vacuum chamber has an arcuate, elongate entrance opening 71 (FIGS. 3 and 4) underlying the rim 45 of the drum 41 and a corresponding arcuate segment of the forming path P. Each vacuum chamber communicates with the foraminous forming surface 11 moving along that segment of the path P via the openings 47 in the rim 45 of the drum. To provide an air resistant seal between the rim 45 and the entrance openings 71 of the vacuum chambers VC1–VC4, rim seals 75 are mounted on the inward-facing surface of the rim 45 for sliding, sealing engagement with the side walls 63 of the vacuum chambers VC1–VC4. Seals (not shown) are also mounted on the partitions or end walls 67 for sliding, sealing engagement with the inward-facing surface of the rim 45. The seals may be formed of a suitable material such as felt to permit the sliding, sealing engagements. The structure defining the vacuum chambers VC1–VC4 is supported in a stationary position by one or more braces 79 mounted on a supporting surface 81 (FIG. 3).

In the embodiment shown, the first and third vacuum chambers VC1–VC3 extend along segments of the forming path P corresponding to the first forming chamber 7; the second vacuum chamber VC2 extends along a segment of the forming path P corresponding to the second forming chamber 9; and the fourth vacuum chamber VC4 extends along a segment of the forming path downstream of second forming chamber 9. The absolute and relative lengths of the segments can vary depending on various factors, to be discussed hereinafter.

Each vacuum source VS1–VS4 also includes an air handling mechanism for generating a vacuum in the respective vacuum chamber. In one embodiment, each such mechanism comprises an air duct 85 connected at one end to the vacuum chamber and at its other end to a device or system 87 (e.g., exhaust fan and motor) for generating an air flow out of the vacuum chamber. It is preferable (although not essential) that each air handling mechanism be adjustable to vary the air flow in its respective vacuum chamber independently of the other vacuum chambers, so that the vacuum in each such chamber may be adjusted as needed or desired. Appropriate controls (e.g., dampers, variable speed fans, etc.) for effecting this adjustment are well known in the art and thus will not be described in detail.

The first forming chamber 7 comprises one or more walls 95 configured to define an interior volume to which the forming surface 11 is exposed upon movement of the forming surface within the forming chamber to form the first layer L1 of the article 3. The second forming chamber 9 is similarly constructed to have walls 99 which define an interior volume to which the forming surface 11 is exposed upon movement of the forming surface within the forming chamber to form the second layer L2 of the article 3. The forming chambers 7, 9 are supported by one or more suitable support frames (not shown) which may be anchored and/or joined to other suitable structural components, as necessary or desirable.

Each of the first and second fiber feed mechanisms 21, 35 comprises a conventional source of fibrous material which delivers a fluent fibrous material (e.g., a flow of discrete fibers) into a respective forming chamber 7, 9. The specific fiber feed mechanisms used may vary, depending on various factors, including the type of fiber being introduced into the chamber. Of course, the type of fiber introduced will depend on the desired composition of the layer formed in the chamber. Typically, fibers of different types will be introduced into the first and second chambers 7, 9, but the same type of fiber can be introduced into both chambers, if desired. By way of example, the first fiber feed mechanism 21 may comprise a conventional fiberizer operatively positioned to deliver fibers into the first chamber 7 through a first fiber inlet 101, and the second fiber feed mechanism 35 may comprise a conventional rotary hammer mill or rotatable picker roll operatively positioned to deliver fibers into the second chamber 9 through a second fiber inlet 105. However, it is to be understood that fluent fibrous material may be delivered to the interiors of the forming chambers 7, 9 in other ways by other suitable devices (e.g., unbailing systems, carding systems, reclaiming systems and other bulk dispensing mechanisms such as those available from Fibercontrols, a business having offices in Gastonia, N.C.) without departing from scope of this invention. As an example, suitable fiberizers and/or hammer mills are available from Paper Converting Machine Company, a business having offices located in Green Bay, Wis., U.S.A.

The fibrous material may include natural fibers, synthetic fibers and combinations thereof. Examples of natural fibers include cellulosic fibers (e.g., wood pulp fibers), cotton fibers, wool fibers, silk fibers and the like, as well as combinations thereof. Synthetic fibers can include rayon fibers, polyolefin fibers, polyester fibers and the like, and combinations thereof. The fibrous materials employed in the apparatus of FIG. 1 may be derived, for example, from batts B of fibers fed to the fiber feed mechanisms 21, 35 where the batts are converted into discrete fibers and delivered through the fiber inlets 101, 105 of the forming chambers 7, 9.

Each of the first and second superabsorbent material (SAM) feed mechanisms 25, 37 comprises a conventional source of SAM which delivers the fluent material into a respective forming chamber 7, 9. For example, particles or fibers of superabsorbent material may be introduced into the forming chambers by employing conventional mechanisms such as pipes, channels, spreaders, nozzles and the like, as well as combinations thereof. In the illustrated embodiment, superabsorbent material is delivered into the first forming chamber 7 by a delivery conduit and nozzle system (which is shown schematically in FIG. 1 and indicated at 25), and superabsorbent material is delivered into the second forming chamber 9 by a delivery conduit and nozzle system (also shown schematically in FIG. 1 and indicated at 37). Typically, different superabsorbent materials will be introduced into the first and second chambers, but the same materials can be introduced into both chambers, if desired. Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

Examples of techniques for introducing a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The fibers, particles and other desired material may be entrained in any suitable fluid medium within the forming chambers 7, 9. Accordingly, any reference herein to air as being the entraining medium should be understood to be a general reference which encompasses any other operative entraining fluid.

The use of two independent forming chambers 7, 9, independent fiber feed mechanisms 21, 35 and SAM feed mechanisms 25, 37 allows independent control over the composition and configuration of the first and second layers being formed. The extent or reach of each forming chamber 7, 9 along the arcuate forming path P is determined by the desired mass flow or basis weight (g/m$^2$) within each of the first and second layers L1, L2 and by the so-called "clean-wire" effect, which is the tendency of fibers and other materials to build up on the foraminous forming surface 11 more quickly toward the beginning of the forming path P. As the forming surface 11 (e.g., wire screen) enters the first forming chamber 7, the foraminous forming areas 61 are empty or clean and thus there is very little resistance to the flow of air through these areas. As a result, the initial rate of material build-up on the forming surface is relatively fast. However, as the thickness of material deposited on the surface increases, the rate of air flow and material build-up decreases. Consequently, the length of the first forming chamber 7 and its matching vacuum chambers (e.g., first and third vacuum chambers VC1, VC3) can be significantly smaller than the length of the second forming chamber 9 (and any later chambers). By way of example, the first forming chamber 7 is preferably 10% to 75% of the total forming chamber length along forming path P, more preferably 10% to 60% of the total forming chamber length, and even more preferably 10% to 50% of the total forming chamber length. Actual forming lengths of the chambers 7, 9 are determined by air flow requirements of the fiber feed mechanisms 21, 35.

In the embodiment shown in FIG. 1, the forming length of the first forming chamber 7 represents approximately 20–30% of the total outer circumference of the drum 41 and corresponds to an angle of about 90 degrees, for example, and the forming length of the second forming chamber 9 represents approximately 33–50% of the total outer circumference of the drum 7 and corresponds to an angle of about 150 degrees, for example.

Figure 2:
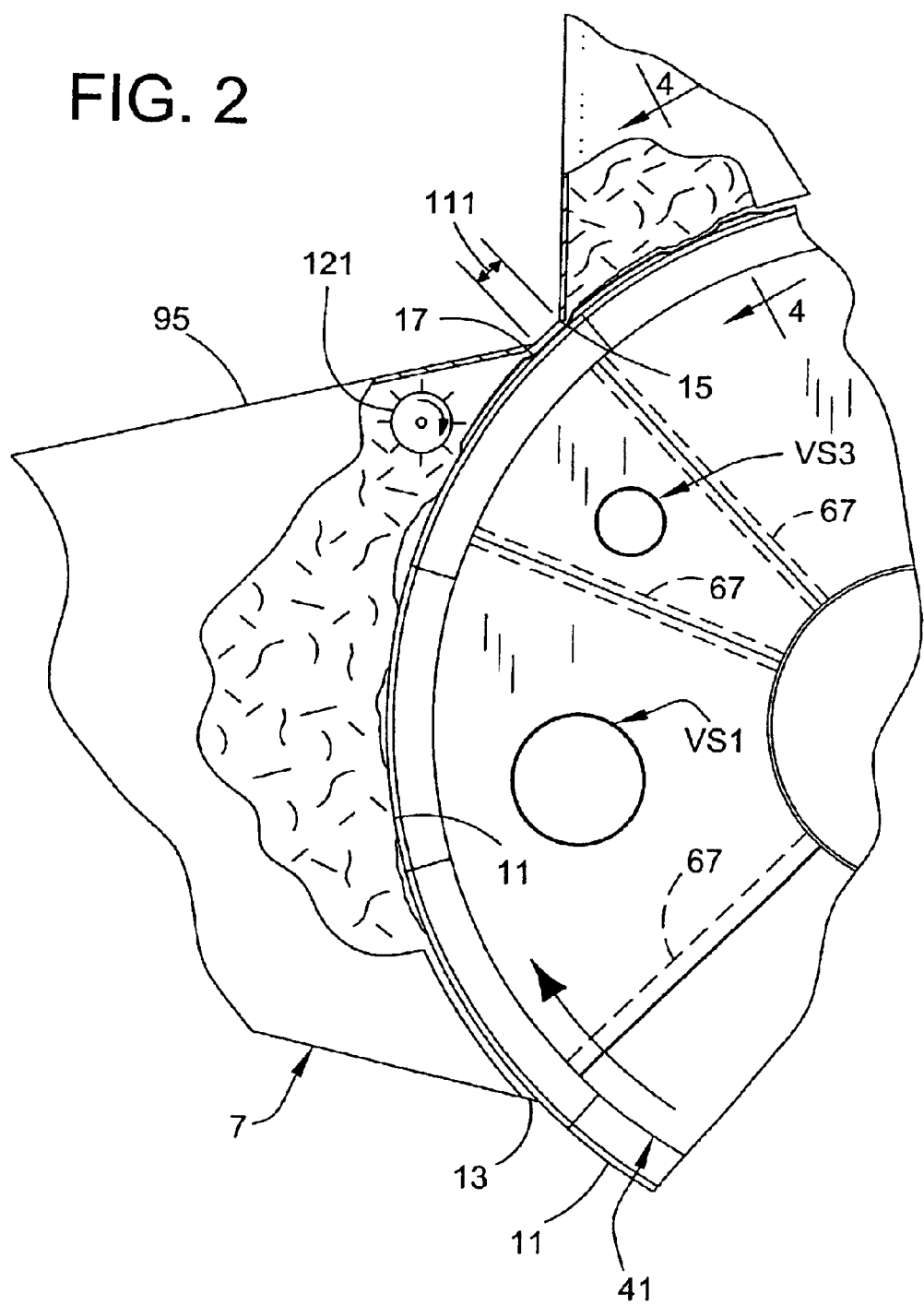
FIG. 2 is an enlarged side elevation of a portion of the apparatus of FIG. 1 with parts broken away to show details.

To prevent any substantial commingling of the fibers and superabsorbent materials in the respective forming chambers 7, 9, and to prevent air leakage from one forming chamber to another chamber, it is preferable that the first and second forming chambers be substantially discrete or separate, meaning that the two chambers are completely separate or at least substantially separate. As used in this context, "substantially" means that any connecting space or passage between the two chambers should have a cross sectional area taken in any plane generally perpendicular to the forming surface 11 no greater than about 200 cm$^2$. (31 in$^2$), and more preferably no greater about 100 cm$^2$ (15 in$^2$), thus avoiding any substantial flow air between the chambers. Even more preferably, the first and second chambers 7, 9 are separated from one another by a zone of separation 111 along the forming path P (see FIG. 2). The length of this zone 111 should be minimized, if possible, so as not to significantly reduce the forming areas within the forming chambers. In this regard, the zone of separation 111 is preferably in the range of 1% to 25% of overall length of the forming path P, more preferably in the range of 1% to 15% of such overall length, and even more preferably in the range of 1% to 5% of the overall length of the forming path P.

In the embodiment of FIG. 1, the foraminous forming surface 11 travels through the zone of separation 111 after it exits the first forming chamber 7 and before it enters the second forming chamber 9. As illustrated, the forming path P in this zone is open to atmosphere and free of enclosure. However, it will be understood that this area could be enclosed in a suitable housing which may be separate from the forming chambers 7, 9 or an integral part of one or both forming chambers. Suitable sealing devices (not shown) are provided at the entrances 13, 15 and exits 17, 19 of the forming chambers for inhibiting the leakage and/or commingling of air, fibers and/or superabsorbent materials from the two forming chambers. Such devices may include sealing rolls, sealing strips, or other conventional devices well known in the art.

The apparatus 1 also includes a first removing and directing mechanism 121 for removing a portion of the first layer L1 and directing the portion removed back into the first forming chamber 7. In the preferred embodiment, this mechanism comprises a rotatable scarfing roll (also designated 121) mounted adjacent the forming path P, generally toward the exit 17 of the first forming chamber 7. The roll 121 is operatively connected and joined to a suitable shaft member (not shown), and is driven by a suitable drive system (not shown). The drive system may include any conventional apparatus, such as a dedicated motor, or a coupling, gear or other transmission mechanism operatively connected to the motor or drive mechanism used to rotate the forming drum 7.

The scarfing roll 121 (or other removal mechanism) has a cutting or abrasive surface suitable for removing material, and it is spaced from the forming surface 11 a distance generally corresponding to the desired thickness T1 (FIGS. 7–9) of the first layer L1 above the forming surface in the Z direction. Upon rotation, the scarfing roll 121 contacts the upper surface of the first layer L1 (i.e., the surface away from the forming surface 11) and removes any material beyond the desired thickness, thereby leveling the first layer prior to its entry into the second forming chamber 9. The rotational speed of the scarfing roll 121 should be suitably selected to provide an effective scarfing action against the contacted surface of the layer. In like manner, any other suitable trimming mechanism may be employed in place of the scarfing roll to provide a cutting or abrading action to the fibrous layer L1 by relative movement between the absorbent member and the selected trimming mechanism.

The spacing between the scarfing roll 121 and the forming surface 11 is preferably adjustable in conventional fashion, so that the thickness T1 of the first layer L1 in the Z direction can be varied, as desired. It is also preferable that the material removed be directed back into the first forming chamber 7 to preserve mass flow, meaning that all of the material, including fibers and superabsorbent materials, delivered to the first chamber are used to form the first layer. This allows the basis weight of the first layer formed in the first forming chamber to be closely controlled. This closed loop mass flow system can be achieved in different ways.

As shown in FIG. 1, for example, the removing and directing mechanism 121 is located inside the forming chamber 7 generally toward the exit 17 of the chamber and functions to throw or "kick back" the removed material into the forming chamber so that it can be redeposited on the forming surface 11. If a rotary mechanism such as the scarfing roll 121 is used to trim layer L1, it is preferable that the mechanism rotate in a direction counter to the direction of movement of the forming surface so that the removed material is directed back in a direction away from the exit 17 of the chamber 7. Alternatively, the removing and directing mechanism 121 can be located outside the forming chamber 7 and include a suitable conveyor 123 for returning the removed material back to the first chamber (see FIG. 1A). For example, a vacuum source such as a fan can be implemented to pneumatically convey the removed material back to the forming chamber directly or to the fiber feed mechanism 21 for re-introduction into the forming chamber 7.

Figure 7:
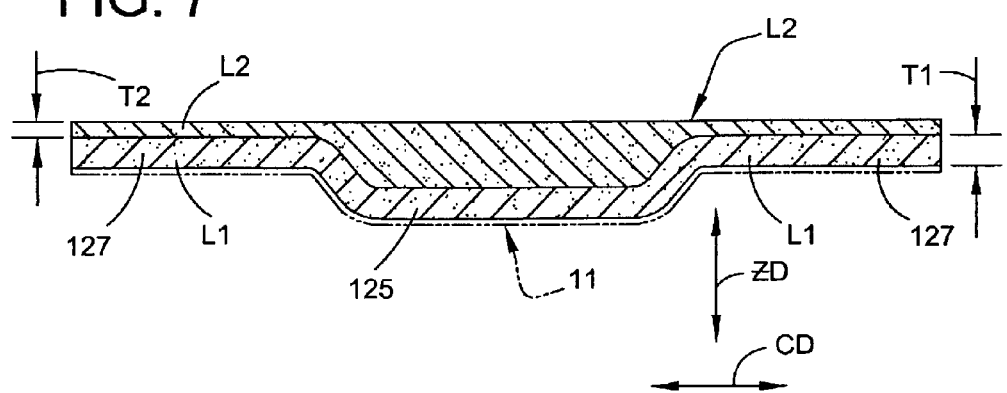
FIGS. 7–9 are sectional views showing variations in the layers of an article formed by the apparatus of FIG. 1.
Figure 8:
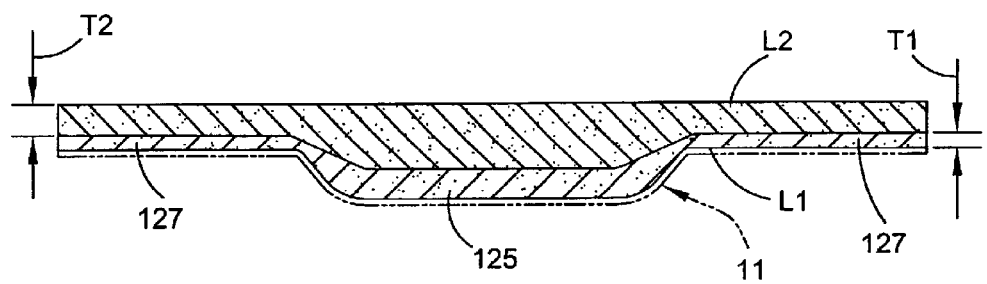
Figure 9:
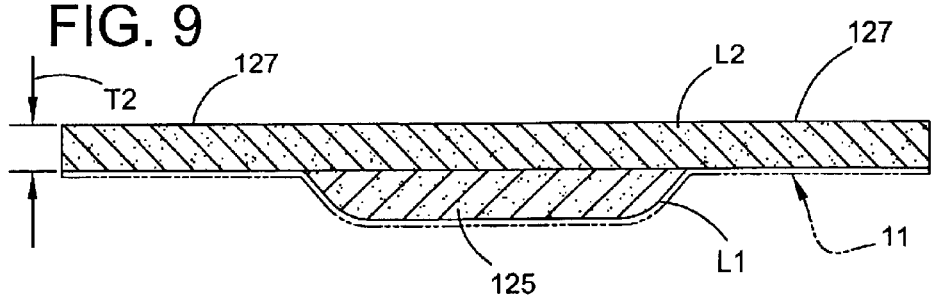

The removing and directing mechanism 121 described above allows the distribution of material in the first layer L1 to be closely controlled in the cross-machine and Z directions CD, ZD. Examples of different distribution patterns are shown in FIGS. 7–9, which illustrate variations of a two-layer absorbent article 3 having a central liquid holding formation 125 over the second (pocket) section 61B of a respective forming area 61 and a pair of ears 127 extending laterally from the central formation over the first section 61A of the forming area. FIG. 7 shows a variation where the gap between the removal mechanism (e.g., scarfing roll 121) and the forming surface has been set to be relatively large (e.g., 0.25 in.) so that only a small amount of material is removed from the first layer L1. As a result, the first layer L1 has a width in the cross-machine direction CD corresponding to the full width of the two-layer article and a relatively large generally uniform thickness (e.g., 0.25 in.) in the Z direction ZD across the entire width of the first and second sections 61A, 61B of the forming area 61. FIG. 8 shows a variation where the gap between the removal mechanism 121 and the forming surface 11 has been reduced (e.g., to 0.125 in.) so that a moderate amount of material is removed from the first layer L1. Consequently, the layer has the same width as FIG. 7 but a reduced thickness T1 (e.g., 0.125 in.) in the Z direction across the first section 61A of the forming area at the ears 127 and an increased thickness across the second (pocket) section 61B in the area of the central formation 125. FIG. 9 shows a variation where the gap between the removal mechanism 121 and the forming surface 11 has been substantially eliminated so that a heavy amount of material is removed from the first layer L1. As a result, the layer L1 is completely removed in the first section 61A of the forming area at the ears 127 and has an even greater thickness in the Z direction across the second (pocket) section 61B at the central formation 125. In this case, a mechanism 121 such as a brush roll should be used to avoid damage to the forming surface 11. Note that as more and more material is removed from layer L1 across the first section 61A of the forming area 61 at the ears 127, the mass distribution of the first layer L1 becomes more and more concentrated across the pocket section 61B at the central formation 125 so that the thickness in this area in the Z direction increases. Thus, the closed-loop mass flow system of the present invention allows close control over the mass distribution of the first layer L1.

Figure 1B:
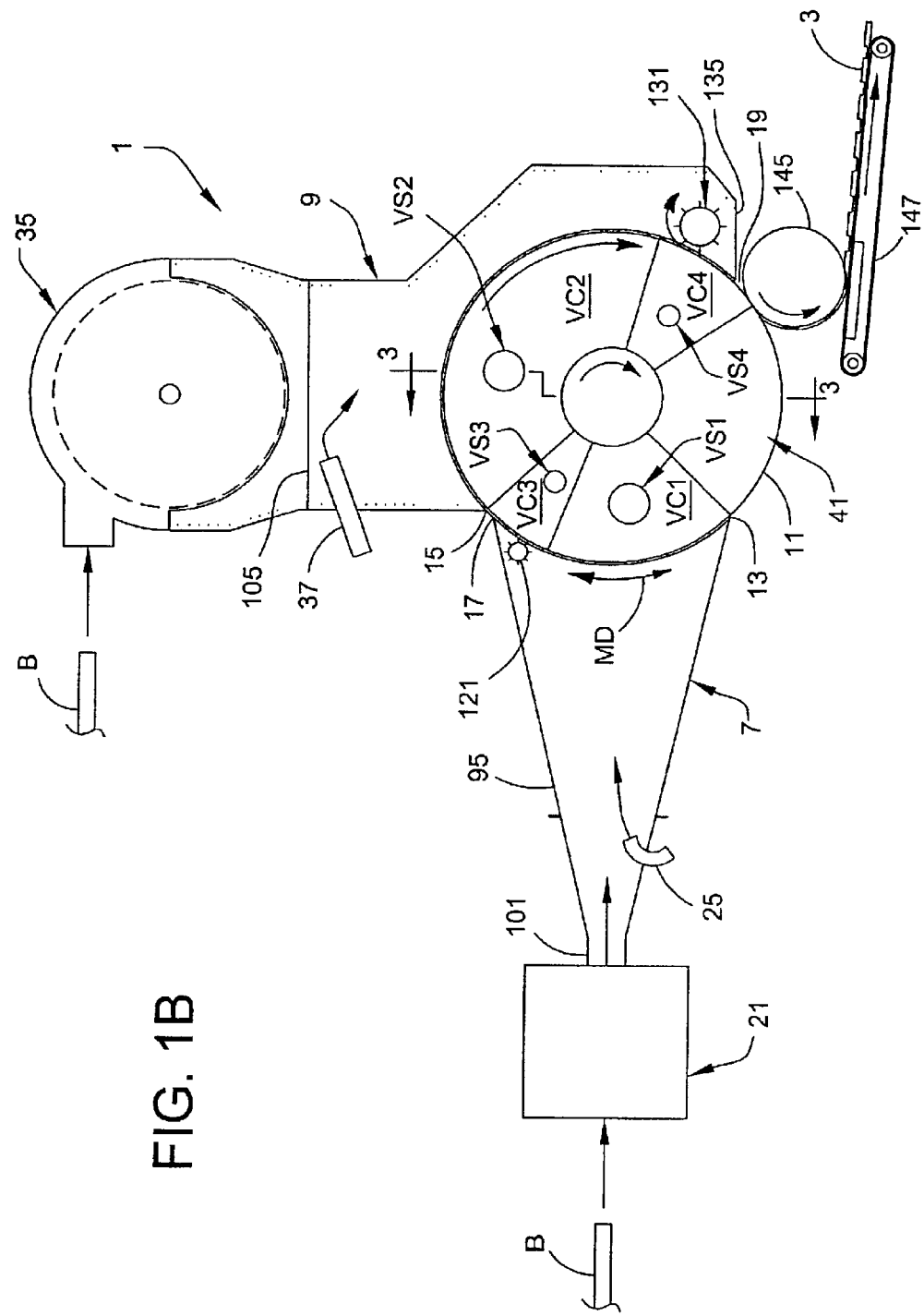
FIG. 1B is a view similar to FIG. 1 but showing a third embodiment of the apparatus.

Referring again to FIG. 1, a second removing and directing mechanism, generally designated 131, is provided for removing a portion of the second layer L2 and directing the portion removed back into the second forming chamber 9. Thus, like the first removing and directing mechanism 121, the second mechanism 131 is a closed-loop mass flow system and it has the same advantages discussed above regarding the first removing and directing mechanism. In the embodiment illustrated in FIG. 1, the mechanism 131 comprises a scarfing roll mounted immediately downstream of the exit 19 of the second forming chamber 9. Like the scarfing roll 121 previously described, the second scarfing roll 131 has a cutting or abrasive surface suitable for removing material from the second layer L2, and the roll is spaced from the forming surface 11 a distance generally corresponding to the desired combined thicknesses T1, T2 of the first and second layers above the forming surface in the Z direction (see FIGS. 7–9). Upon rotation, the roll 131 contacts the upper surface of the second layer L2 (i.e., the surface away from the foraminous forming surface 11) and removes any material beyond the desired thickness. Devices other than a scarfing roll may be used to remove this excess material from the second layer. The second removing and directing mechanism 131 also includes a pneumatic conveyance system 133 comprising, in one embodiment, a housing 135 for the roll and a duct 139 connected to the housing for pneumatically conveying the removed material back to the second forming chamber 9. The air stream in the duct 139 may be generated by an exhaust fan or other suitable means (not shown). Alternatively, the second removing and directing mechanism 131 may be located inside the second forming chamber 9, preferably toward the exit 19 of the chamber, much like the first removing and directing mechanism 121 is located toward the exit 17 of the first forming chamber 7 (see FIG. 1B).

In general, a "kick-back" removal and directing mechanism 121 of the type described above in connection with the first forming chamber 7 is preferred where relatively small amounts of material are to be removed. Where heavier amounts are to be removed, it may be preferable to use a removal and directing mechanism (e.g., 131) which includes a separate conveyance system (e.g., system 133 shown in FIG. 1) for conveying the removed material back to the appropriate forming chamber. For further details regarding exemplary systems, reference may be made to pending U.S. patent application Ser. No. 09/840,384 entitled METHOD AND APPARATUS FOR GEOMETRIC SCARFING by Joseph m. Kugler et al., filed Apr. 23, 2001.

Referring to FIG. 1, the four vacuum chambers VC1–VC4 are arranged so that the first and second chambers VC1, VC2 communicate with the first and second forming chambers 9, 11, respectively. In the illustrated embodiment, the first vacuum chamber VC1 extends along a first arcuate segment from the entrance 13 of the first forming chamber 7 to a location generally upstream of the first removing and directing mechanism 121; the second vacuum chamber VC2 extends along a second arcuate segment from the entrance 15 of the second forming chamber 9 to the exit 19 of the second forming chamber; the third vacuum chamber VC3 extends between the first and second forming chambers 7, 9 along a third arcuate segment from adjacent or upstream of the first removing and directing mechanism 121, past the zone of separation 111 to the entrance 15 of the second forming chamber 9; and the fourth vacuum chamber VC4 extends from the exit 19 of the second forming chamber to a location downstream of the second removing and directing mechanism 131 generally corresponding to a rotatable vacuum transfer cylinder 145 which functions to transfer articles from the drum to a suitable conveyor 147 or other location for further processing of the articles. As described above, the vacuums in the various vacuum chambers VC1–VC4 are preferably capable of independent adjustment so that the degree of vacuum in each chamber can be independently varied as needed. By way of example, the vacuums in the first and second vacuum chambers VC1, VC2 should be sufficient (e.g., in the range of from −20 to −30 in. water) to produce first and second layers L1, L2 of the required thicknesses and mass distributions, and the vacuums in the third and fourth vacuum chambers VC3, VC4 should be sufficient (e.g., in the range of from −15 to −20 in. water) to hold the materials on the forming surface 11 as material is removed by the removing and directing mechanisms 121, 131. The interior space of the drum between the fourth and first vacuum chambers is preferably not under vacuum. Optionally, the fourth vacuum chamber could be divided into two sections, the first section being located on the arcuate segment of drum corresponding to the removing and directing mechanism 131 and the second section being located downstream from the first generally in the area of the transfer cylinder 145. In this configuration, the vacuum in the second section preferably would be less (e.g., −5 to −7 in. water) than the vacuum in the first section to facilitate transfer of the articles 3 from the drum to the cylinder.

In operation, the air handling mechanisms 87 are operated to establish vacuums of appropriate magnitude in respective vacuum chambers VC1–VC4 to create air flows through the forming surface 11. Further, the first and second fiber feed mechanisms 21, 35 and first and second superabsorbent material feed mechanisms 25, 37 are operated to introduce selected fibers and selected superabsorbent materials into respective first and second chambers 7, 9 at the desired rates to form the first and second layers L1, L2 of the articles 3 to be made. (Additional forming chambers and associated equipment can be provided to form additional layers, if desired.) The gaps between the scarfing rolls 121, 123 and the forming surface 11 are also adjusted to provide the desired thicknesses and contours.

As the forming surface 11 enters and then moves through the first forming chamber 7 along the forming path P toward the exit of the chamber 17, the fluidized fibers and superabsorbent materials within the forming chamber are operatively carried or transported by an entraining air stream and drawn inward by the vacuum toward the forming surface 11. Air passes inward through the foraminous areas 61 of the surface 11 and is subsequently passed out of the drum 41 through the vacuum ducts 85. Fibers and other particulates are collected by the forming surface 11 as the air passes therethrough such that the collection of fibrous material forms a first layer L1 of material on the foraminous areas 61 of the forming surface. As the layer passes the first removal and directing mechanism (e.g., the first scarfing roll 121), excess thickness of the layer L1 is trimmed and removed to an extent determined by the gap between the removal mechanism and the forming surface 11. The removed material is returned to the first forming chamber 7 either directly by "kick-back" or by a separate return system as previously discussed.

Subsequently, the drum 41 carrying the trimmed first layer L1 exits the first forming chamber 7, passes through the separation zone 111 and enters the second forming chamber 9 where the fibers and superabsorbent material in the chamber are vacuum drawn toward the forming surface and deposited on the first layer L1 to form the second layer L2. As they are deposited, the fibrous material of the second layer becomes entangled and otherwise commingles with the fibrous material of the first layer, thereby improving fluid transfer between the layers. Further, because the two forming chambers are independent, the first and second layers L1, L2 are always in proper phase (registration) with one another. After exiting the second forming chamber 7, the forming surface 11 passes beneath the second scarfing roll 131 which functions to remove or trim any excess portions of the second layer L2, as needed. The removed material is conveyed back to the second forming chamber 9 by the pneumatic conveyance system 133.

Following the second scarfing operation, the forming surface 11 on which the two-layer articles 3 are formed moves to a release zone of the apparatus 1 disposed exterior of the forming chambers. In the release zone, the articles are transferred by the vacuum transfer cylinder onto the conveyor 147, which may be a vacuum conveyor for facilitating the transfer to the conveyor. Alternatively, the articles 3 may be transferred directly to the conveyor without an intervening transfer cylinder. The release of the articles 3 can be assisted by the application of air pressure from the interior of the drum 41. The conveyor 147 receives the formed articles 3 and conveys the them to a collection area or to a location for further processing (not shown). Suitable conveyors can, for example, include conveyer belts, vacuum drums, transport rollers, electromagnetic suspension conveyors, fluid suspension conveyors or the like, as well as combinations thereof. Removal of the articles 3 from the forming surface 11 can alternatively be accomplished by the weight of the articles, by centrifugal force, by mechanical ejection, by positive air pressure or by some combination thereof or by another suitable method without departing from the scope of this invention. As an example, the removed articles 3 of the illustrated embodiment are interconnected as a series of articles, each of which has a selected surface contour that substantially matches the contours provided by the corresponding foraminous areas 61 of the forming surface 11 upon which the articles are formed.

It will be readily apparent that various conventional devices and techniques can be employed to further process the articles after removal from the drum 41. For example, the articles can be compressed at a debulking station. In addition, various conventional devices and techniques can be employed to sever the articles 3 into predetermined lengths to provide selected air formed fibrous absorbent members for example. The severing system may, for example, include a die cutter, a water cutter, rotary knives, reciprocating knives, energy beam cutters, particle beam cutters or the like, as well as combinations thereof. After severing, the discrete articles 3 can be transported and delivered for further processing operations, as desired.

The apparatus and process described above are effective for the manufacture of a multiple-layer fibrous articles while maintaining close control of the fiber and SAM concentrations within each layer, and while providing consistent weight variability to the finished articles. The flexibility of the system allows the mass flow rate of fibrous material and superabsorbent material (if used) to be varied between forming chambers. For example, fibrous materials may be introduced into the first and second forming chambers at first and second mass flow rates, respectively, with the first rate being greater than or less than the second rate. Similarly, superabsorbent materials may be introduced into the first and second forming chambers at first and second mass flow rates, respectively, with the first rate being greater than or less than the second rate. The single-drum, multiple forming chamber system disclosed herein is more economical than two or more independent forming systems and eliminates the possibility of "out-of-phase" defects and waste associated with such independent systems. The teachings of the present invention may also facilitate the retrofitting of a single forming system into a multiple forming system by nature of its favorable space requirements, thus allowing the manufacturing conversion to take place in less time and for less capital.

The product benefits of the process of the present invention include the capability of achieving any SAM mixing distribution desired, including homogeneous, layered or stratified. Further, the SAM distributions can be similar or different between layers. This flexibility allows for product enhancements such as a dedicated fluid intake and fluid distribution layers. Using multiple SAMS and/or multiple fibers can also be beneficial from a grade cost standpoint because high performance and high cost materials can be deployed more judiciously.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for air forming an article having a plurality of superimposed fibrous layers, said apparatus comprising:
    first and second substantially discrete forming chambers,
    a foraminous forming surface movable through said first and second forming chambers along a forming path length,
    a first fiber feed mechanism for introducing a fibrous material into said first forming chamber,
    a first vacuum source in communication with said first forming chamber for drawing said fibrous material in said first forming chamber onto said forming surface to form a first layer on said forming surface,
    a first removing and directing mechanism for removing a portion of said first layer and directing the portion removed back into said first forming chamber,
    a second fiber feed mechanism for introducing a fibrous material into said second forming chamber, and
    a second vacuum source in communication with said second forming chamber for drawing said fibrous material in said second forming chamber onto said forming surface to form a second layer on said forming surface superimposed on said first layer.

2. Apparatus as set forth in claim 1 further comprising a first superabsorbent feed mechanism for introducing a superabsorbent material into said first forming chamber.

3. Apparatus as set forth in claim 2 further comprising a second superabsorbent feed mechanism for introducing a superabsorbent material into said second forming chamber.

4. Apparatus as set forth in claim 1 wherein said forming surface is on a drum rotatable to move the forming surface through said first and second forming chambers along an arcuate forming path length.

5. Apparatus as set forth in claim 4 wherein said first and second forming chambers are separated from one another by a zone of separation along said arcuate forming path length.

6. Apparatus as set forth in claim 5 wherein said zone of separation is no greater than 25% of the forming path length.

7. Apparatus as set forth in claim 5 wherein said zone of separation is no greater than 5% of the forming path length.

8. Apparatus as set forth in claim 4 wherein said first vacuum source comprises a first vacuum chamber inside the drum extending over a first arcuate segment of said arcuate path length and a first air handling mechanism for establishing a first vacuum in said first vacuum chamber; and wherein said second vacuum source comprises a second vacuum chamber inside the drum extending over a second arcuate segment of said arcuate path length and a second air handling mechanism for establishing a second vacuum in said second vacuum chamber.

9. Apparatus as set forth in claim 8 wherein said first and second air handling mechanisms are independently adjustable to vary the air flow through the respective vacuum chambers.

10. Apparatus as set forth in claim 8 further comprising a third vacuum source for holding said first layer on said forming surface as said portion of the first layer is removed by said first removing and directing mechanism, said third vacuum source comprising a third vacuum chamber inside the drum extending over a third arcuate segment of said arcuate path length between said first and second arcuate segments, and a third air handling mechanism for establishing a third vacuum in said third vacuum chamber.

11. Apparatus as set forth in claim 10 wherein said first, second and third air handling mechanisms are independently adjustable to vary the air flow through the respective vacuum chambers.

12. Apparatus as set forth in claim 1 wherein said first removing and directing mechanism is located inside said first forming chamber.

13. Apparatus as set forth in claim 1 wherein said first removing and directing mechanism is located outside said first forming chamber.

14. Apparatus as set forth in claim 1 further comprising a second removing and directing mechanism for removing a portion of said second layer and directing the portion removed back into said second forming chamber.

15. Apparatus as set forth in claim 14 further comprising a vacuum source for holding said first and second layers on said forming surface as said portion of the second layer is removed by said second removing and directing mechanism, said vacuum source for holding said first and second layers comprising a vacuum chamber inside the drum extending over an arcuate segment of said arcuate path length downstream of said second arcuate segment, and an air handling mechanism for establishing a vacuum in said vacuum chamber.

16. Apparatus as set forth in claim 14 wherein said second removing and directing mechanism is located outside said second forming chamber and comprises a conveyor system for delivery of said removed portion back to said second forming chamber.

17. Apparatus as set forth in claim 14 wherein said second removing and directing mechanism is located inside said second forming chamber.

18. Apparatus as set forth in claim 1 wherein said first and second fiber feed mechanisms are operable to introduce different fibrous materials into respective forming chambers.

19. Apparatus as set forth in claim 3 wherein said first and second superabsorbent feed mechanisms are operable to introduce different superabsorbent materials into respective forming chambers.

20. Apparatus as set forth in claim 1 wherein the first forming chamber extends along a shorter segment of the forming path length than said second forming chamber.

21. Apparatus as set forth in claim 1 wherein said first forming chamber extends along 10–50% of the combined lengths of said first and second forming chambers along said forming path length.

22. Apparatus as set forth in claim 1 wherein said forming surface has a plurality of foraminous areas spaced at intervals along the forming surface, each foraminous area having a first section for collecting fibrous material to a first depth and a second section for collecting fibrous material to a second depth greater than said first depth, said first removing and directing mechanism being adapted to remove material from said first layer on the first section of each foraminous area and to direct it back to the first forming chamber for deposit on other foraminous areas thereby to increase the depth of the first layer in said second sections of said foraminous areas.

23. Apparatus as set forth in claim 22 wherein said first removing and directing mechanism is operable to remove substantially all of the first layer in said first section of each foraminous area.

24. A process of forming an article having a plurality of superimposed fibrous layers, said process comprising:
   moving a foraminous forming surface through first and second substantially discrete forming chambers along forming path length,
   introducing a fibrous material into said first forming chamber,
   vacuum drawing said fibrous material in said first forming chamber onto said forming surface to form a first layer on said forming surface,
   removing a portion of said first layer and directing the portion removed back into said first forming chamber,
   introducing a fibrous material into said second forming chamber, and
   vacuum drawing said fibrous material in said second forming chamber onto said forming surface to form a second layer on said forming surface superimposed on said first layer.

25. A process as set forth in claim 24 further comprising introducing a superabsorbent material into said first forming chamber.

26. A process as set forth in claim 25 further comprising introducing a superabsorbent material into said second forming chamber.

27. A process as set forth in claim 26 further comprising introducing different superabsorbent materials into said first and second forming chambers.

28. A process as set forth in claim 26 wherein superabsorbent material is introduced into the first forming chamber at a first mass flow rate and superabsorbent material is introduced into the second forming chamber at a second mass flow rate greater than said first mass flow rate.

29. A process as set forth in claim 26 wherein superabsorbent material is introduced into the first forming chamber at a first mass flow rate and superabsorbent material is introduced into the second forming chamber at a second mass flow rate less than said first mass flow rate.

30. A process as set forth in claim 24 wherein fibrous material is introduced into the first forming chamber at a first mass flow rate and fibrous material is introduced into the second forming chamber at a second mass flow rate greater than said first mass flow rate.

31. A process as set forth in claim 24 wherein fibrous material is introduced into the first forming chamber at a first mass flow rate and fibrous material is introduced into the second forming chamber at a second mass flow rate less than said first mass flow rate.

32. A process as set forth in claim 24 wherein said forming surface is on a drum, said process further comprising rotating the drum to move the forming surface along an arcuate forming path length.

33. A process as set forth in claim 32 wherein said first and second chambers are separated from one another by a zone of separation along said arcuate path length.

34. A process as set forth in claim 32 further comprising establishing a vacuum in a first vacuum chamber inside the drum, said first vacuum chamber communicating with said first forming chamber and extending over a first arcuate segment of said arcuate path length and establishing a vacuum in a second vacuum chamber inside the drum, said second vacuum chamber communicating with said second forming chamber and extending over a second arcuate segment of said arcuate path length.

35. A process as set forth in claim 34 further comprising independently adjusting the air flow through said first and second vacuum chambers.

36. A process as set forth in claim 34 further comprising establishing a vacuum in a third vacuum chamber inside the drum extending over a third arcuate segment of said arcuate path length between said first and second arcuate segments for holding said first layer on said forming surface as said portion of the first layer is removed by said first removing and directing mechanism.

37. A process as set forth in claim 24 wherein said portion of the first layer is removed inside said first forming chamber.

38. A process as set forth in claim 24 wherein said portion of the first layer is removed outside said first forming chamber.

39. A process as set forth in claim 24 wherein said forming surface has a plurality of foraminous areas spaced at intervals along the forming surface, each foraminous area having a first section for collecting fibrous material to a first depth and a second section for collecting fibrous material to a second depth greater than said first depth, and wherein said removing and directing step comprises removing material from said first layer on the first section of each foraminous area and directing it back to the first forming chamber for deposit on other foraminous areas thereby to increase the depth of the first layer in said second sections of said foraminous areas.

40. A process as set forth in claim 39 further comprising removing substantially all of the first layer in said first section of each foraminous area.

41. A process as set forth in claim 24 further comprising removing a portion of said second layer and directing the portion removed back into said second forming chamber.

42. A process as set forth in claim 41 wherein said forming surface is on a drum, and wherein said process further comprises rotating the drum to move the forming surface along an arcuate forming path length, and establishing a vacuum in a vacuum chamber inside the drum extending over an arcuate segment of said arcuate path for holding said first and second layers on said forming surface as said portion of the second layer is removed.

43. A process as set forth in claim 42 wherein said portion of said second layer is removed outside said second forming chamber and directed back to said second forming chamber.

44. A process as set forth in claim 42 wherein said portion of said second layer is removed inside said second forming chamber and directed back to said second forming chamber.

45. A process as set forth in claim 24 further comprising adjusting the air flow in said first and second vacuum chambers to vary the vacuum in each vacuum chamber independent of the other vacuum chamber.

46. A process of forming an article having a plurality of superimposed fibrous layers, said process comprising:

moving a foraminous forming surface through first and second substantially discrete forming chambers along an arcuate forming path length, said forming surface having a plurality of foraminous areas spaced at intervals along the forming surface, each foraminous area having a first section for collecting fibrous material to a first depth and a second section for collecting fibrous material to a second depth greater than said first depth, introducing a fibrous material into said first forming chamber, vacuum drawing said fibrous materiai in said first forming chamber onto said forming surface to form a first layer on said first and second sections of said forming areas, introducing a fibrous material into said second forming chamber, and vacuum drawing said fibrous material in said second forming chamber onto said forming surface to form a second layer on said first and sections of said forming areas superimposed on said first layer.

\* \* \* \* \*